(12) United States Patent
Boehm et al.

(10) Patent No.: US 7,378,401 B2
(45) Date of Patent: May 27, 2008

(54) USE OF FOSFLURIDINE TIDOXIL (FT) FOR THE TREATMENT OF INTRAEPITHELIAL PROLIFERATIVE DISEASES

(75) Inventors: Erwin Boehm, Ladenburg (DE); Michael Kulke, Ludwigshafen (DE); Eggert Stockfleth, Albersdorf (DE)

(73) Assignee: Heidelberg Pharma GmbH, Ladenburg (DE)

( * ) Notice: Subject to any disclaimer, the term of this patent is extended or adjusted under 35 U.S.C. 154(b) by 189 days.

(21) Appl. No.: 11/486,376

(22) Filed: Jul. 14, 2006

(65) Prior Publication Data

US 2008/0014258 A1  Jan. 17, 2008

(51) Int. Cl.
*A01N 43/04* (2006.01)
*A61K 31/70* (2006.01)
*C07H 19/04* (2006.01)
*C07H 19/20* (2006.01)

(52) U.S. Cl. .......................... 514/46; 514/43; 514/45; 514/47; 514/49; 514/50; 514/51; 514/885; 514/908; 536/26.7; 536/26.8

(58) Field of Classification Search ...................... None
See application file for complete search history.

(56) References Cited

U.S. PATENT DOCUMENTS 6,025,343 A * 2/2000 Herrmann et al. ............ 514/46

2005/0090659 A1  4/2005 Herrmann

FOREIGN PATENT DOCUMENTS

EP  1 229 040 A2  8/2002

OTHER PUBLICATIONS

Anonymous, "Phase II study intitiated with oral fosfluridine in actinic keratosis" [Online], Aug. 16, 2005, Retrieved from Internet: URL: www.bioportfolio.com/aug_05/17_08_2005.

Joseph L. Jorizzo, "Current and Novel Treatment Options for Actinic Keratosis", Incorporating Medical and Surgical Dermatology, vol. 8, No. 3, Dec. 1, 2004, pp. 13-21.

Heidelberg Pharma AG, "Fosfluridine Tidoxil shows effectivness in Actinic Keratosis", [Online] May 17, 2007, Retrieved from Internet: www.heidelberg-pharma.com/new/popup/20.

* cited by examiner

*Primary Examiner*—Patrick T Lewis
(74) *Attorney, Agent, or Firm*—Rothwell, Figg, Ernst & Manbeck, P.C.

(57) ABSTRACT

The present invention is directed to the systemic administration of Fosfluridine Tidoxil, (5-fluorouridine)-5'-phosphoric acid (3-dodecylmercapto-2-decyloxy)propylester or a salt thereof, for the treatment of intraepithelial proliferative diseases such as actinic keratosis. The Fosfluridine Tidoxil can be systemically administered alone or in combination with topical treatment agents.

13 Claims, No Drawings

USE OF FOSFLURIDINE TIDOXIL (FT) FOR THE TREATMENT OF INTRAEPITHELIAL PROLIFERATIVE DISEASES

DESCRIPTION OF INVENTION

The subject of the present invention is the use of Fosfluridine Tidoxil (FT), for the systemic treatment of intraepithelial proliferative disease, especially of actinic keratosis.

BACKGROUND

Actinic Keratosis (AK) is a carcinoma in situ of the epidermis, an early stage of squamous cell carcinoma (Guidelines for the Management of Actinic Keratoses, Subcommittee of the European Dermatology Forum, 2004/2005). Actinic keratosis often develops in fair-skinned people, particularly in regions of the earth with high UV irradiation. In the US actinic keratoses are the most common premalignant lesions in humans. The incidence is much higher in the Sun Belt and is directly related to light skin and sun exposure. In a study performed in Great Britain, 15% of all men and 6% of all women were affected (Memon A A, Tomenson J A, Bothwell J, Friedmann P S. Prevalence of solar damage and actinic keratosis in a Merseyside population: Br J Dermatol 2000; 142: 1154-1159). The prevalence in Australia is even higher. In approximately 10% of all patients with actinic keratosis and approximately 30% of patients with actinic keratosis and additional immune suppression, the progression to an invasive squamous cell carcinoma at a later stage occurs. In order to avoid this progression an efficient treatment is required.

The current treatments for actinic keratosis consist basically of operative and physical methods and topical pharmacological therapy options. Possible treatments include cryosurgery (freezing), surgical excision, curettage (scraping) with or without electrosurgery (heat generated by an electric current) and topical (applied to the skin) medications. Lasers, chemical peels, dermabrasion, and photodynamic therapy may also be used. Unfortunately, operative and physical methods frequently cause serious adverse reactions and often have a high rate of relapse. Diclofenac-Hyaluronic-Acid (Solaraze®), 5-Fluorouracil and Imiquimod are currently available as topical pharmacological therapies for early stages of AK. Retinoids which could be administered orally against actinic keratosis are not authorized on the German market due to their very serious adverse reactions. The rate of full recovery when using topical therapies is only about 50%. In addition to this moderate success rate, subclinical manifestations of actinic keratosis (frequently occurring in addition to visible lesions) can trigger relapses. They are not visible and therefore the cream is often not applied to them. A further disadvantage of topical application is the fact that the agents must be administered for long periods of time and after a certain time patient compliance decreases. For example, a cream like Imiquimod has to be administered for up to 16 weeks.

The current treatments for actinic keratosis are therefore unsatisfactory and prior to the present invention, there was no adequate oral treatment for actinic keratosis. This is particularly bad in the treatment of advanced actinic keratosis, for which the topical treatments seem to be even less effective

BRIEF SUMMARY OF THE PRESENT INVENTION

Surprisingly, cytological studies have shown that FT is far more effective in proliferating primary human keratinocytes compared to non-proliferating keratinocytes. As the tolerability of orally administered FT has been proven in an oncological study, the substance was administered orally in patients suffering from actinic keratosis. In this trial it was demonstrated that FT is beneficial in the systemic treatment of actinic keratosis. Therefore, for the first time a tolerable systemic treatment option for actinic keratosis in general and for advanced actinic keratosis in particular is available.

FT [chemical name: (5-fluorouridine)-5'-phosphoric acid (3-dodecylmercapto-2-decyloxy)propylester, Na-salt] is the subject of the U.S. Pat. No. 6,025,343 which is hereby incorporated by reference. FT is suitable in therapy and prophylaxis of malignant tumors and exhibits immunosuppressive activity. FT is administered preferably orally as tablets or capsules, and has at least a comparable efficacy and lower toxicity in comparison to the parent compound 5-Fluorouridine (5-FUrd) and 5-FU. It has therefore a wider therapeutic range.

5-FU is being used in the therapy of actinic keratosis but only topically. Due to the side effects and pharmacokinetics, 5-FU cannot be administered systemically in the treatment of intraepithelial proliferative diseases. Furthermore, the therapeutic effect of topical 5-FU is limited in advanced stages of actinic keratosis. In contrast, orally administered FT was found beneficial in the treatment of advanced stages of actinic keratosis which is believed to be representative of intraepithelial proliferative diseases.

DETAILED DESCRIPTION OF THE INVENTION

Fosfluridine (FT) is comprised of a specific carrier molecule, coupled through a phosphate group to 5-Fluorouridine (5-FUrd), an active metabolite of 5-Fluorouracil (5-FU). FT enters the system at the FUrdMP site and the active principle 5-Flurouridine-triphosphate (FUrdTP) is formed. FT is pharmacologically inert, has no or insignificant first pass effect, does not show cleavage in the serum, has little distribution in the bone marrow, has a long half-life, a good tolerability and a good oral bioavailability.

5-FU is used e.g., for palliative treatment of breast, colorectal, gastric and pancreatic cancer. In contrast to FT, limitations in the therapy with 5-FU arise from safety concerns, in particular bone marrow toxicity. Absorption of 5-FU after oral administration is erratic and unpredictable, therefore 5-FU is administered intravenously. 5-FU has a short biological half-life of 6-20 minutes. Over 90% of the drug is eliminated within the first hour after intravenous administration, predominantly through enzymatic degradation in plasma and in the liver/other tissues by dihydropyrimidine dehydrogenase (DPD). The response to and clearance of 5-FU is subject to high interindividual variation, which correlates with plasma and tissue DPD activity.

FT showed distinctly superior anti-tumor potency in various animal tumor models, compared with equimolar 5-FU or 5-FUrd doses. For example, Fosfluridine induced a dose-dependent inhibition of SCLC xenograft tumor growth in mice of up to 82%. FT was generally well tolerated. This has been confirmed in acute i.v. and p.o. tolerability studies in mice (no animal died, not even at the highest single p.o. dose tested so far of 3.8 g/kg) and in acute, sub-chronic and chronic GLP toxicity studies in mice, rats and monkeys.

Administration of FT results in intracellular formation of 5-Fluorouridine-monophosphate which is then di- and triphosphorylated. Triphosphorylated 5-Fluorouridine is the active metabolite of 5-Fluorouracil, which is currently in use for intravenous treatment of patients with oncological indications. One of the drawbacks of using intravenously administered 5-Fluorouracil is bone marrow suppression, expressed clinically by increased susceptibility to infections and fatigue. Orally administered FT has the advantage of having less side effects with preserved effectiveness, compared to intravenous 5-Fluorouracil, in particular with respect to bone marrow suppression, as well as offering more convenience to both physicians and patients. From preclinical data it is known that Fosfluridine does not penetrate into the bone marrow.

In contrast to 5-FUrd, which dose-dependently suppressed bone marrow cells, single and repeated intravenous doses of FT did not result in bone marrow toxicity. This may be explained, at least in part, by the observation that FT is not distributed to the bone marrow and that it did not suppress in vitro colony formation of CFU-E and CFU-GM at doses manifold higher than highly toxic doses of FUrd.

FT's plasma half-life after oral administration to mice is 4-5 h, in rhesus monkeys 8-10 h and in man >20 h. This is significantly longer than the biological half-life of less than 30 minutes for 5-FU and 5-FUrd. Plasma concentrations correlate linearly with administered doses. FT catabolism, and accordingly its anti-tumor activity, is independent of DPD. Plasma concentrations of 5-FU and 5-FUrd in man were negligible after administration of FT. This can be explained, at least in part, by the high plasma stability of FT and bioactivation only within the cell to release 5-FUrd-monophosphate.

FT may be administered in combination with other drugs for the treatment and prophylaxis of intraepithelial proliferative diseases. Examples of these further drugs include but are not limited to antiproliferative or immunemodifying drugs e.g. vinblastine, alkylating cytostatic agents such as cyclophosphamide, melphalan, myleran or cisplatin, antimetabolites such as folic acid antagonists (methotrexate) and antagonists of purine and pyrimidine bases (mercaptopurine, 5-fluorouridine, cytarabin), cytostatically active antibiotics such as anthracyclines (e.g., doxorubicin, daunorubicin), hormones such as fosfestrol, tamoxifen, other cytostatically/cytotoxically active chemotherapeutic agents, other immunosuppressive drugs (such as cyclosporines, FK 506, rapamycines, desoxyspergualin, etc.). Preferred combination partners are diclofenac-hyaluronic acid, 5-fluorouracil and imiquimod.

Preferred salts of FT are the alkali, alkaline earth and ammonium salts of the phosphate group. Preferred as the alkali salts are lithium, sodium and potassium salt. Possible as the alkaline earth salts are magnesium and calcium, in particular. According to the invention, ammonium salts are understood to be those containing the ammonium ion which may be substituted up to four times by alkyl residues having 1-4 carbon atoms, and/or aralkyl residues, preferably benzyl residues. Here, the substituents may be the same or different.

FT may be administered in liquid or solid form using the intestinal or parenteral route. Any suitable application forms can be used, including but not limited to tablets, capsules, coated tablets, syrups, solutions, or suspensions. The solid dosage forms may be prepared in layers or coated with suitable coatings to provide sustained release dosage forms. Preferably, water is used as the injection medium, containing additives such as stabilizers, solubilizers and buffers as are common with injection solutions. Such additives are, e.g., tartrate and citrate buffers, ethanol, complexing agents such as ethylenediaminetetraacetic acid and its non-toxic salts, high-molecular polymers such as liquid polyethylene oxide for viscosity control. Liquid vehicles for injection solutions need to be sterile and are filled in ampoules, preferably. Solid carriers include but are not limited to starch, lactose, mannitol, methylcellulose, talc, highly dispersed silicic acids, higher-molecular fatty acids such as stearic acid, gelatine, agar-agar, calcium phosphate, magnesium stearate, animal and plant fats, solid high-molecular polymers such as polyethylene glycol, etc. If desired, formulations suitable for oral application may include flavorings or sweeteners.

FT may be administered to any mammal in need of treatment. The dosage will depend on various factors such as mode of administration, animal species, age, or individual condition. For the treatment of actinic keratosis, FT is administered in amounts of 0.1-500 mg, preferably 50-150 mg. The preferred route of administration is oral. FT can be administered orally in combination with topical administration of FT or another suitable drug. The daily dose can be divided into 2-5 applications, with tablets having an active ingredient content of 0.5-500 mg being administered with each application. Similarly, the tablets may have sustained release, reducing the number of applications to 1-3 per day. The active ingredient content of sustained-release tablets may be 2-1000 mg. The active ingredient may also be administered by continuous infusions, where amounts of 5-1000 mg per day are normally sufficient. Preferably a single dose of 50-150 mg is administered once a day for 7 days followed by a 7 day therapy free interval, this cycle is preferably repeated at least 3 times. The minimum number of cycles for effective treatment is 2 cycles. The cycles may be repeated for up to one year.

FT can be used in the treatment of intraepithelial proliferative diseases including but not limited to actinic keratosis, Cervical intraepithelial neoplasia (CIN), valvular intraepithelial neoplasia (VIN), vaginal intraepithelial neoplasia (VaIN), anal intraepithelial neoplasia (AIN) and any carcinoma in situ.

The following examples are illustrative of the present invention, but should not be considered as limiting the scope of the invention in any way, as these examples, and other equivalents thereof, will become apparent to those skilled in the art in the view of the present disclosure.

EXAMPLE 1

Preparation of 2',3'-Isopropylidene-5-fluorouridine 262 g (1 mol) 5-Fluorouridine and 7.5 g (0.04 mol) p-toluene sulfonic acid monohydrate were stirred and heated to reflux in 2.5 l acetone. After addition of 120 ml dimethoxypropane within 10 minutes reflux was continued for 90 minutes. Subsequently, 2.5 l isohexane were slowly added over a time period of 25-30 minutes to the hot solution, which resulted in crystallization. The suspension was cooled to 0-2° C. and stirred at this temperature for further 60 minutes. The precipitate was isolated by filtration and washed with cold isohexane.

The solid was dried in vacuo at 40° C. for 24 hours to give 276 g (91%) product.

EXAMPLE 2

Preparation of 5-Fluoro-5'-uridylic acid, mono[2-(decyloxy)-3-(dodecylthio)propyl]ester calcium salt 129.0 g (260 mmol) of phosphoric acid, (2-decyloxy-3-dodecylthio)propyl ester and 157.3 g (520 mmol) of 2,4,6-triisopropylbenzenesulfonyl chloride were dissolved in 2.5 l dry pyridine and stirred for two hours at 20-25° C. in an atmosphere of nitrogen. After addition of 78.6 g (260 mmol) 2',3'-isopropylidene-5-fluorouridine in one portion, stirring was continued for further 16 hours at 20-25° C.

Subsequently, the mixture was treated with 5 ml demineralized water, stirred for further 15 minutes and the solvent was removed at a maximum temperature of 60° C. in vacuo. The residue was treated three times with 400 ml of toluene and evaporated to dryness. The residual viscous oil was treated with 4 l of methyl-tert-butyl ether at 40° C. and the suspension was stirred for 30 minutes. The precipitated salt was separated by filtration and washed with 300 ml methyl-tert-butyl ether. The filtrate was washed with 800 ml of 3 N hydrochloric acid and the organic layer was evaporated in vacuo. The residue was co-evaporated with methanol (2 l), redissolved in 2 l methanol and treated under vigorous stirring with a solution of 49.2 g calcium acetate in 150 ml demineralized water at room temperature. The suspension was stirred at 20-25° C. for one hour. The precipitate was isolated by filtration and washed with 200 ml methanol. The salt was dried for 24 hours at 50° C. in vacuum to give 191.3 g crude calcium salt.

19.13 g of the crude calcium salt were suspended in 200 ml methyl-tert-butyl ether, 120 ml 3 N hydrochloric acid were added and the mixture was stirred until the precipitate was dissolved. The aqueous layer was removed and the organic layer was evaporated to give viscous oil. The residue was dissolved in 50 ml methanol, 1 g Luvocell in 100 ml mobile phase (methanol/0.04 M sodium acetate buffer 87.5/12.5) were added and the suspension was stirred for 15 minutes at 20-30° C. The pH was adjusted to 5.5 by addition of 5.4 ml triethylamine and the suspension was filtered through a bed of 1 g reversed phase silica gel (Merck, LiChroprep RP 18, 15-25 pm). The filter was washed with 10 ml mobile phase and the combined filtrates were purified by preparative HPLC on LiChroprep RP 18, 15-25 pm with methanol/0.04 M sodium acetate buffer 87.5/12.5 (v/v).

The product containing fractions were collected and concentrated in vacuo at max. 40° C. to ⅙ of the starting volume. Calcium acetate (4.60 g) in 15 ml demineralized water was added and the suspension was stirred at 0° C. for 4 h. the product was filtered off, washed with 50 ml acetone and dried (13.85 g pure Ca salt).

The phosphoric acid, (2-decyloxy-3-dodecylthio)propyl ester was prepared as described in WO 92/03462.

EXAMPLE 3

Preparation of 5-Fluoro-5'-uridylic acid, mono[2-(decyloxy)-3-(dodecylthio)propyl]ester sodium salt 13.43 g calcium salt (product of example 2) were suspended in 150 ml methyl-tert.-butyl ether and 85 ml 3 N hydrochloric acid were stirred until all of the precipitate was dissolved. The organic phase was separated, extracted a second time with 85 ml 3 N hydrochloric acid and the solvent was stripped off. The residue was twice dissolved in 45 ml toluene and evaporated to dryness. Subsequently, the residue was dissolved in 30 ml toluene, the solution was passed through a filter and adjusted to a pH of 7.0 by addition of 3.7 sodium methylate solution (30% in methanol). The toluene solution was slowly added under stirring at 20-25° C. to 220 ml acetone. The formed suspension was stirred for 30 minutes at 20-25° C., cooled to 0-5° C. and stirred for 1 hour at a temperature below 5° C. The precipitate was filtered off, washed with 45 ml cold acetone and dried in vacuo to give 13.25 g sodium salt (67% based on 2',3'-Isopropylidene-5-fluorouridine).

EXAMPLE 4

Manufacturing of Capsules

| Capsules (Hard Shell) | |
|---|---|
| Ingredient | approx. quantity/capsule/mg |
| Povidone | 6.6 |
| Lactose, Monohydrate | 75.0 |
| Croscarmellose Sodium | 13.0 |
| Fosfluridine Tidoxil | 50.0 |
| Colloidal Silicon Dioxide | 12.0 |
| Cellulose, Microcrystalline | 35.4 |
| Starch | 2.0 |
| Sodium Lauryl Sulfate | 4.0 |
| Magnesium Stearate | 2.0 |
| Total | 200.0 |

| Manufacturing Process | |
|---|---|
| Step 1 | Lactose, monohydrate and part of the croscarmellose sodium are sieved and mixed. |
| Step 2 | Povidone is solved in purified water. |
| Step 3 | The mixture obtained in step 1 is granulated with the solution obtained in step 2 in a suitable wet granulator. |
| Step 4 | Fosfluridine Tidoxil and part of the colloidal silicon dioxide are sieved and added to the granule obtained in step 3. |
| Step 5 | The granules are sieved and dried. |
| Step 6 | Microcrystalline cellulose, starch, sodium lauryl sulfate, croscarmellose sodium (remaining and colloidal silicon dioxide (remaining) are sieved and mixed. |
| Step 7 | The mixture obtained in step 6 is added to the granules obtained in step 5. |
| Step 8 | Magnesium stearate is sieved and added to the mixture obtained in step 7. |
| Step 9 | The mixture obtained in step 8 is mixed. |
| Step 10 | The mixture obtained in step 9 is filled into hard gelatin capsules. |

EXAMPLE 5

Manufacturing of Tablets

| Tablets (Core) | | |
|---|---|---|
| | approx. quantity/capsule | |
| Ingredient | Example I/mg | Example II/mg |
| Fosfluridine Tidoxil | 50.0 | 50.0 |
| Cellulose, Microcrystalline | 117.2 | 184.5 |
| Starch | 13.0 | 16.0 |
| Sodium Lauryl Sulfate | 4.0 | 8.0 |
| Crospovidone | 22.0 | 32.0 |
| Colloidal Silicon Dioxide | 9.5 | 8.0 |

-continued

| Tablets (Core) | | |
|---|---|---|
| Lactose, Monohydrate | 106.7 | 30.5 |
| Povidone | 24.1 | 17.5 |
| Magnesium Stearate | 3.5 | 3.5 |
| Total | 350.0 | 350.0 |

Manufacturing process I:

- step 1  Lactose, monohydrate, fosfluridine tidoxil and part of the crospovidone are sieved and mixed
- step 2  Povidone is solved in purified water
- step 3  The mixture obtained in step 1 is granulated with the solution obtained in step 2 in a suitable wet granulator
- step 4  The granules obtained in step 3 are sieved and dried.
- step 5  Microcrystalline cellulose, starch, sodium lauryl sulfate, crospovidone (remaining), and colloidal silicon dioxide are sieved and mixed.
- step 6  The mixture obtained in step 5 is added to the granules obtained in step 4.
- step 7  Magnesium stearate is sieved and added to the mixture obtained in step 6.
- step 8  The mixture obtained in step 7 is mixed.
- step 9  The mixture obtained in step 8 is formed into tablets by means of a rotary tabletting press.

Manufacturing process II:

- step 1  Fosfluridine Tidoxil, povidone and part of the colloidal silicon dioxide are sieved and mixed.
- step 2  Microcrystalline cellulose, starch, lactose monohydrate, sodium lauryl sulfate, crospovidone, and colloidal silicon dioxide (remaining) are sieved and mixed.
- step 3  The mixture obtained in step 1 is added to the mixture obtained in step 2.
- step 4  The mixture obtained in step 3 is sieved and mixed.
- step 5  Magnesium stearate is sieved and added to the mixture obtained in step 4.
- step 6  The mixture obtained in step 5 is mixed.
- step 7  The mixture obtained in step 6 is formed into tablets by means of a rotary tabletting press.

EXAMPLE 6

Administration of Fosfluridine Tidoxil in the Treatment of Actinic Keratosis

EXAMPLE 6A

A 70 years old man was suffering from an advanced actinic keratosis since more than 3 years. In this time he received different types of topical treatment, such as Solaraze (3% Diclofenac) or Aldara (Imiquimod). Thereafter he was treated with 50 mg of Fosfluridine Tidoxil (1 capsule). The patient received 3 cycles each cycle consisting of a once daily oral administration over 7 days followed by a treatment free week (two weeks per cycle). After 6 weeks of treatment and another month of observation it was found that the lesion count was reduced by 34%. The severity of the lesions as indicated by histological assessment was reduced from stage 3 to stage 1 in the most severe area each. Surprisingly it was found that this patient responded stronger after the administration of Fosfluridine Tidoxil on topical treatment than before.

EXAMPLE 6B

A 64 years old male patient was diagnosed to have an actinic keratosis 15 years before and was now in an advanced stage. In the years before taking Fosfluridine Tidoxil he was, in essence, treated with Solaraze. Since the therapeutic benefit appears to be limited he then received 100 mg of oral Fosfluridine Tidoxil (2 capsules of 50 mg) over 3 cycles (as mentioned above).

After one further months of observation he was found to have a reduction in lesion count by 22% and the histological stage decreased from class 2 to class 1. Thereafter he received, again, Solaraze over 12 weeks and responded dramatically, in contrast to the previous use of Solaraze. At the end of this follow-up treatment all actinic keratoses have disappeared. Obviously, Fosfluridine Tidoxil sensitized the patient for Solaraze.

EXAMPLE 6C

A 70 years old man with a first diagnosis of Actinic keratosis 1.6 years before use of Fosfluridine Tidoxil was treated topically, however, eventually without therapeutic benefit. The disease proceeded in an advanced stage. He then received 100 mg of oral Fosfluridine Tidoxil (2 capsules of 50 mg) over 3 cycles (as described above). After treatment and one month of observation his histological stage was reduced from class 3 to class 2 and the lesion count was reduced by 45%. This patient was not treated over the next four months with any topical. Nevertheless, all actinic keratoses have disappeared.

EXAMPLE 6D

A 79 years old patient suffered from Actinic keratosis for more than 7 years and was now in an advanced stage. He had not received any treatment during this period. He, then, received 100 mg of oral Fosfluridine Tidoxil (2 capsules of 50 mg) over 3 cycles (as de-scribed above). After an additional one month observation period the lesion count was reduced by 9% and the histological stage was reduced from 3 to 1. In the next 2 month this patient was not treated with any topical. Again, it could be observed that all actinic lesions have disappeared within this period.

We claim:

1. A method for treating an intraepithelial proliferative disease comprising systemically administering to a patient in need of such treatment an amount of (5-fluorouridine)-5'-phosphoric acid (3-dodecylmercapto-2-decyloxy)propylester or a salt thereof, effective to treat said intraepithelial proliferative disease.

2. The method according to claim 1, wherein said intraepithelial proliferative disease is actinic keratosis.

3. The method according to claim 2, wherein said (5-fluorouridine)-5'-phosphoric acid (3-dodecylmercapto-2-decyloxy)propylester or a salt thereof is administered orally.

4. The method according to claim 3, wherein said (5-fluorouridine)-5'-phosphoric acid (3-dodecylmercapto-2-decyloxy)propylester or a salt thereof is administered as a single daily dose.

5. The method according to claim 4, wherein said (5-fluorouridine)-5'-phosphoric acid (3-dodecylmercapto-2-decyloxy)propylester or a salt thereof is in the form of a sustained release tablet or capsule.

6. The method according to claim 3, wherein said (5-fluorouridine)-5'-phosphoric acid (3-dodecylmercapto-2-decyloxy)propylester or a salt thereof is administered as multiple doses daily.

7. The method according to claim 3, wherein said 5-fluorouridine)-5'-phosphoric acid (3-dodecylmercapto-2-decyloxy)propylester or a salt thereof is administered daily in an amount of 0.1-100 mg per kg of body weight.

8. The method according to claim 7, wherein said 5-fluorouridine)-5'-phosphoric acid (3-dodecylmercapto-2-decyloxy)propylester or a salt thereof is administered daily in an amount of 0.2-80 mg per kg of body weight.

9. The method according to claim 1, wherein said 5-fluorouridine)-5'-phosphoric acid (3-dodecylmercapto-2-decyloxy)propylester or a salt thereof is administered in combination with another antiproliferative or immune modifying drug.

10. The method according to claim 9, wherein said antiproliferative or immune modifying drug is administered simultaneously or subsequently.

11. The method according to claim 9, wherein said antiproliferative or immune modifying drug is selected from the group consisting of diclofenac-hyaluronic acid, 5-fluorouracil and imiquimod.

12. The method according to claim 1, wherein said patient is a human.

13. The method according to claim 1, wherein said salt of (5-fluorouridine)-5'-phosphoric acid (3-dodecylmercapto-2-decyloxy)propylester is an alkali, alkaline earth or ammonium salt of the phosphate group.

* * * * *